US006548556B2

(12) United States Patent
Hobson et al.

(10) Patent No.: US 6,548,556 B2
(45) Date of Patent: Apr. 15, 2003

(54) STABLE ENZYMATIC WOUND DEBRIDER

(75) Inventors: David W. Hobson, San Antonio, TX (US); David P. Jones, San Antonio, TX (US); Katarzyna Koster, San Antonio, TX (US); Pilar P. Duque, San Antonio, TX (US)

(73) Assignee: Healthpoint, Ltd., San Antonio, TX (US)

( * ) Notice: Subject to any disclaimer, the term of this patent is extended or adjusted under 35 U.S.C. 154(b) by 32 days.

(21) Appl. No.: 09/749,217

(22) Filed: Dec. 27, 2000

(65) Prior Publication Data

US 2002/0114798 A1 Aug. 22, 2002

(51) Int. Cl.[7] .................. A61K 47/32; A61K 31/74; A61K 38/54; A61K 38/46; A61K 38/43
(52) U.S. Cl. ................. 514/772.4; 424/78.06; 424/94.1; 424/94.21; 424/94.3; 424/94.65
(58) Field of Search ............... 514/772.4, 458; 424/50, 49, 541, 94.1, 642, 94.4, 643, 702, 78.06, 94.65, 94.3; 604/307, 289, 304

(56) References Cited

U.S. PATENT DOCUMENTS

| 2,917,433 A | 12/1959 | Goldman ................. 167/65 |
| 2,995,493 A | 8/1961 | Douglas et al. .......... 167/73 |
| 3,003,917 A | 10/1961 | Beiler et al. ............. 167/73 |
| 3,019,171 A | 1/1962 | Bloch et al. ............. 195/68 |
| 3,409,719 A | 11/1968 | Noe et al. ................ 424/94 |
| 3,860,702 A | 1/1975 | Buell ...................... 424/94 |
| 3,983,209 A | 9/1976 | Schmitt .................. 424/78 |
| 4,250,167 A | 2/1981 | Davis ..................... 424/94 |
| 4,556,056 A | 12/1985 | Fischer et al. .......... 128/156 |
| 4,668,228 A | * 5/1987 | Bolton et al. ............ 604/307 |
| 4,801,451 A | 1/1989 | Hellgren et al. ......... 424/94.63 |
| 4,963,491 A | 10/1990 | Hellgren et al. ......... 435/264 |
| 5,106,621 A | 4/1992 | Rowan et al. ........... 424/94.65 |
| 5,130,131 A | 7/1992 | Narayanan et al. ...... 424/94.65 |
| 5,206,026 A | 4/1993 | Sharik .................... 424/445 |
| 5,296,222 A | 3/1994 | Petersen et al. ......... 424/94.63 |
| 5,494,896 A | 2/1996 | Hansbrough ............ 514/12 |
| 5,505,958 A | 4/1996 | Bello et al. ............. 424/449 |
| 5,578,310 A | 11/1996 | M'Timkulu et al. ..... 424/401 |
| 5,747,005 A | * 5/1998 | Barels et al. ............ 424/50 |
| 5,840,283 A | 11/1998 | Sorenson et al. ........ 424/61 |
| 6,030,612 A | 2/2000 | de Faire et al. ......... 424/94.63 |
| 6,096,309 A | 8/2000 | Prior et al. ............. 424/94.63 |

FOREIGN PATENT DOCUMENTS

| EP | 0 194 647 A | 9/1986 |
| EP | 0 498 532 A | 8/1992 |
| EP | 0 576 279 A | 12/1993 |
| EP | 0 674 001 A | 9/1995 |
| WO | WO 95 23614 A | 9/1995 |
| WO | WO 98 55604 A | 12/1998 |

* cited by examiner

Primary Examiner—Thurman K. Page
Assistant Examiner—Blessing Fubara
(74) Attorney, Agent, or Firm—McKee, Voorhees & Sease, P.L.C.

(57) ABSTRACT

This invention relates to an enzymatic anhydrous hydrophilic wound debrider that uses in combination a proteolytic enzyme and an anhydrous hydrophilic poloxamer carrier.

14 Claims, 1 Drawing Sheet

STABLE ENZYMATIC WOUND DEBRIDER

FIELD OF THE INVENTION

This invention relates to a composition for the enzymatic debridement of necrotic tissue, and for liquifaction of pus in acute and chronic wounds.

BACKGROUND OF THE INVENTION

Enzymatic wound debridement has been known in the past. However, it has substantial efficacy problems. In particular, prior art wound debridement compositions normally require refrigeration for stable storage, and have shelf life stability problems because they normally contain substantial amounts of water. Water has been thought necessary because it allows dissolving of the enzyme, which in turn was thought necessary in order to have effective wound debridement.

The combination of heat-sensitive proteolytic enzymes and substantial amounts of water-based carriers has provided a net effect of requiring both cold storage temperatures, commonly at refrigeration temperatures, and short shelf life before use. As a result, such compositions have been little used, and have met with less than ideal commercial satisfaction.

It, therefore, can be seen that there is a continuing need for a normal room temperature, low odor, effective proteinase wound debrider, having good shelf life stability at room temperatures that does not sacrifice the debridement effective nature of the proteinase. This invention has as its primary objective the fulfillment of the above-described need.

Another objective of the present invention is to provide a room temperature stable enzymatic wound debrider of a consistency or viscosity that allows the product to stay in wounds that are necrotic and exudating.

Another objective of the present invention is to provide an enzymatic wound debrider of the type meeting the above objectives which can be effectively packaged and dispensed from a tube.

Another objective of the present invention is to provide compositions of the type above-described which can incorporate both anhydrous and hydrophilic components, and the active enzymatic debrider, along with other active ingredients in a unique semisolid ointment dressing to allow for superior room temperature stability for proteinases in general, and for papain in particular.

The method and manner of accomplishing each of the above objectives, as well as others, will become apparent from the detailed description of the invention which follows hereinafter.

SUMMARY OF THE INVENTION

Figure 1:
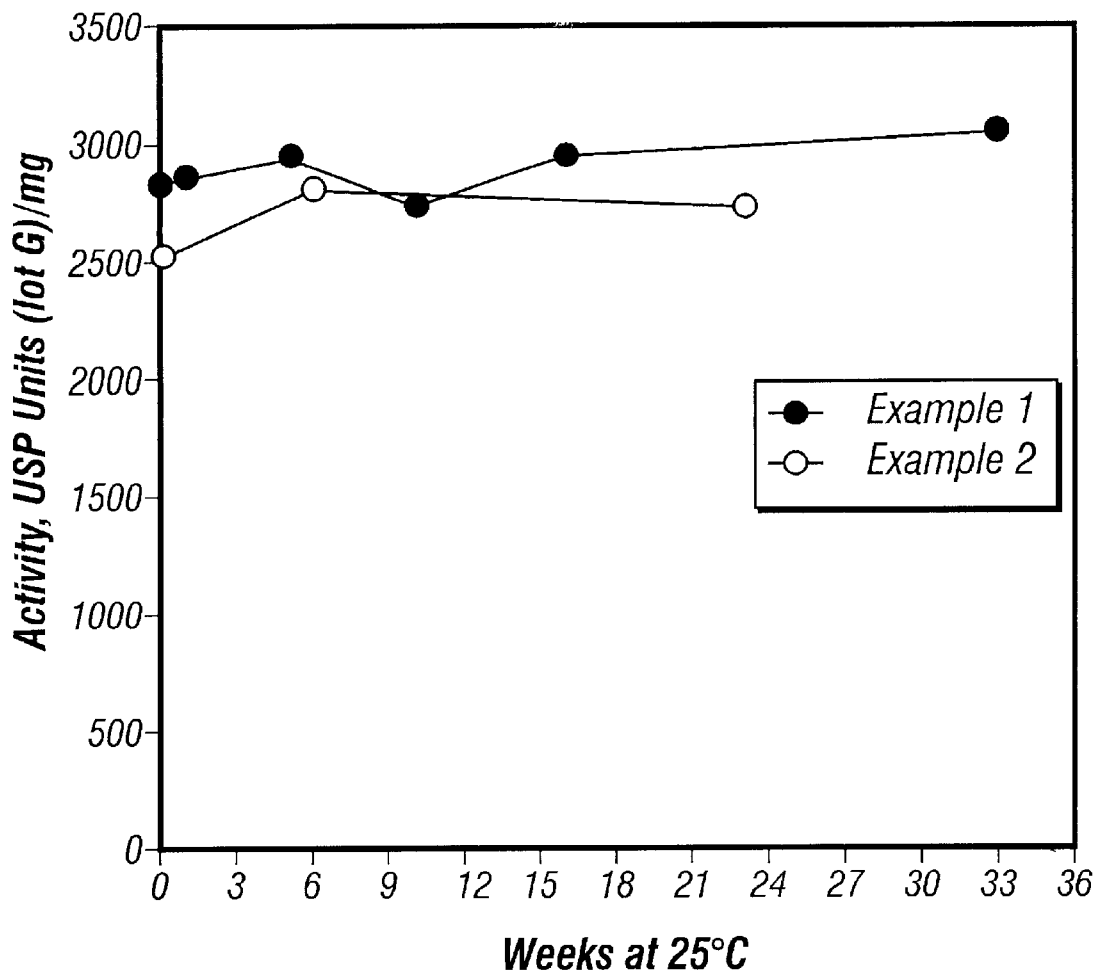
FIG. 1 is a graph showing room temperature papain stability studies.

A semisolid hydrophilic anhydrous ointment enzymatic debridement composition for necrotic wounds designed to have room temperature stability and maintain efficaciousness of the proteinaceous enzyme is disclosed. In the broadest sense, the composition is an enzymatic wound debrider of an anhydrous hydrophilic poloxamer carrier in combination with a small but debridement effective amount of one or more proteolytic enzymes, and preferably papain.

DETAILED DESCRIPTION OF THE PREFERRED EMBODIMENT

The base or carrier portion of the present invention can be generally described as an anhydrous poloxamer carrier, which is a block copolymer of ethylene oxide and propylene oxide of the structure:

$$HO(C_2H_4O)_x(C_3H_6O)_y(C_2H_4O)_xH$$

wherein x is from 2 to 150, and y is from 15 to 70. Preferably x is from 12 to 141, and y is from 20 to 56. Generally speaking, block copolymers of ethylene oxide and propylene oxide meeting the above descriptions are available from BASF sold under the trademark "Pluronic and Lutrol F Block Copolymers". For specifics of such polymers in detail, see BASF Corporation Technical Data Sheets on Pluronic polyols, copyright 1992, the disclosure of which is incorporated herein by reference.

These generally embrace block copolymers having a molecular weight within the range of 1000 to 16,000. Importantly, for the present invention they have water solubility, exist in cream or ointment form, and can be stored for long periods of time in anhydrous conditions.

The useful block copolymers of ethylene oxide and propylene oxide herein generally speaking have a hydrophilic-lipophilic balance (HLB) value within the range of from 8 to 30, and preferably from 12 to 25. Using the poloxamer coding labels of BASF, suitable poloxamers for use in this invention include, but are not limited to:

Pluronic/Lutrol F 44 (poloxamer 124)
Pluronic/Lutrol F 68 (poloxamer 188)
Pluronic/Lutrol F 87 (poloxamer 237)
Pluronic/Lutrol F 108 (poloxamer 338)
Pluronic/Lutrol F 127 (poloxamer 407)

Turning next to the small but debridement effective amount of a proteolytic enzyme. As those skilled in the art know, a proteolytic enzyme will have in part or in total the capacity to hydrolyze peptide amide bonds. Such enzymes may also have some inherent lipolytic and/or amylolitic activity associated with the proteolytic activity. The preferred proteolytic enzyme is papain. Other suitable proteolytic enzymes include trypsin, chymo-trypsin, streptokinase, streptodormase, ficin, pepsin, carboxypeptidase, aminopeptidase, chymopapain, bromelin and other proteolytic enzymes.

Papain is an enzyme derived from the native green fruit of the tropical papaw or melon tree (*Carica papaya*) whose clear watery fluid is collected, dried, powdered, and sieved to produce the papain. It is an enzyme similar to pepsin, but acts in acid, alkaline or neutral solution. It is white to gray powder and is moderately hygroscopic. It dissolves about 200 times its weight of coagulated egg albumin in alkaline liquid in about 5 hrs. It is very soluble in water and glycerine, but almost insoluble in alcohol. High Activity Purified Papain (Belgium), commercially available from Enzyme Development Corporation, is a highly refined papain with a potency of 50,000 USP units/mg. This material is supplied as a white to tan colored powder with low odor.

Prolase 300® protease is commercially available and contains the activated and refined proteolytic enzymes derived from the tropical plant *Carica papaya*. Prolase 300® is supplied as a light tan-colored powder of uniform potency. Each gram of Prolase 300® contains 300 Wallerstein Papain Activity units as determined either by a milk clotting assay method or by a casein digestion method.

Another group of suitable proteolytic enzymes includes those which are substantially free of sulfihydryl groups or disulfide bonds, and include the serine proteases, particularly those derived from Bacillus and Streptomiasis bacteria and aspergilis molds.

Within this latter grouping, the more preferred enzymes are the Bacillus derived alkaline proteases generically called subtilisin enzymes. Reference is made to Deayl, L., Moser, P. W. and Wildi, B. S., "Proteases of the Genus Bacillus. II alkaline Proteases." Biotechnology and Bioengineering, Vol. XII, pp. 213–249 (1970) and Keay, L. and Moser, P. W., "Differentiation of Alkaline Proteases from Bacillus Species" Biochemical and Biophysical Research Comm., Vol. 34, No. 5, pp. 600–604, (1969).

The subtilisin enzymes are broken down into two sub-classes, subtilisin A and subtilisin B. In the subtilisin A grouping are enzymes derived from such species are *B. subtilis, B. licheniformis* and *B. pumilis*. Organisms in this sub-class produce little or no neutral protease or amylase.

In addition, other suitable enzymes are, for example, pancreatin, trypsin, collaginase, keratinase, carboxylase, aminopeptidase, elastase, and aspergillo-peptidase. A and B, pronase E (from *S. griseus*) and dispase (from *Bacillus polymyxa*).

An effective amount of the enzyme is to be used in the practice of this invention. Such amount will be that amount which effectively debrides necrotic tissue and liquefies pus in acute and chronic wounds. Such an amount will also be that amount which effects removal in a reasonable time (for example, over a 7 day period), of substantially all of such materials. The precise amount used for any particular use will depend on several factors, including the inherent activity of the enzyme, the number of applications intended for the wound, etc. As a basic yardstick, the working gel provides an activity between about 500 USP units/mg to 3000 USP units/mg, preferably 800 USP units/mg to 2200 USP units/mg. However, lower amounts may be used. In weight/volume terms, the enzyme preparations are seldom pure, and it is expected that the enzyme source will be used in amounts of from 1% to 15% of the weight of the total gel formulation. Precise amounts will vary with purity of the enzyme.

While not known precisely why this invention combination works better than a prior art, it is believed the following mechanism occurs, which explains the synergy occurring between the anhydrous ointment base and a proteolytic enzyme. Since the base is anhydrous, it enhances stability of the enzyme while the enzyme is mixed with the base and not in contact with any water. When the mixture contacts a wound, the wound contains watery material, and so the anhydrous hydrophilic base material releases the enzymatic material into contact with the watery materials located in the wound to be debrided. The enzyme then attacks the proteinaceous material of the wound, clips off the amino acid ends, breaks down the protein into smaller units, and it can then be easily washed away. All of this occurs as moisture diffuses into the anhydrous hydrophilic base, solubilizing the enzyme.

In contrast with the prior art systems which employ either water-based materials or anhydrous insoluble materials, the enzyme is not, on the one hand, prematurely released as with the water-based materials, or, on the other hand, is held in the bases so tightly that it does not have contact with the wound to effectuate debridement. As a result, the invention formulation is effective where prior enzymatic debriders were generally not.

As those skilled in the art know, the compositions of the present invention may contain other components referred to as minors such as enzymatic activators, wound healing agents, structure-forming ingredients, anti-microbial agents, antibiotic agents, and/or anesthetic agents, all generally from the GRAS safe list. Generally, amounts of these will vary from 0.01% to 25%.

The following in vitro enzymatic activity studies were conducted for laboratory assessment purposes and are predictive of the product's commercial behavior. The following compositions were made:

|  | % w/w |
|---|---|
| EXAMPLE 1 | |
| Poloxamer 407 | 9.8 |
| Poloxamer 338 | 16.1 |
| Poloxamer 124 | 66.6 |
| Papain | 7.5 |
| EXAMPLE 2 | |
| Propylene Glycol | 20.0 |
| Poloxamer 407 | 6.67 |
| Poloxamer 338 | 9.53 |
| Poloxamer 124 | 55.9 |
| Povidone | 0.40 |
| Papain | 7.50 |
| EXAMPLE 3 | |
| Encapsulated Urea | to yield 10% |
| Poloxamer 407 | 6.67 |
| Poloxamer 338 | 9.53 |
| Povidone | 0.40 |
| Papain | 7.50 |
| Poloxamer 124 | qs to 100% |

Room temperature papain stability studies were conducted with the following results as illustrated in FIG. 1.

What is claimed is:

1. An enzymatic wound debrider, consisting essentially of:
   an anhydrous hydrophilic poloxamer carrier, and
   a small but debridement effective amount of one or more proteolytic enzymes.

2. The enzymatic wound debrider of claim 1 wherein the poloxamer carrier is a block copolymer of ethylene oxide and propylene oxide of the structure:

$$HO(C_2H_4O)_x(C_3H_6O)_y(C_2H_4O)_xH$$

wherein x is from 2 to 150, and y is from 15 to 70.

3. The enzymatic wound debrider of claim 2 wherein x is from 12 to 141, and y is from 20 to 56.

4. The enzymatic wound debrider of claim 1 wherein the proteolytic enzyme is used in an amount sufficient to have an activity of from 500 USP units/mg to 3000 USP units/mg.

5. The enzymatic wound debrider of claim 4 wherein the enzymatic activity is from 800 USP units/mg to 2200 USP units/mg.

6. The enzymatic wound debrider composition of claim 1 wherein the proteolytic enzyme is selected from the group consisting of papain, trypsin, chymo-trypsin, streptokinase, streptodornase, ficin, pepsin, carboxypeptidase, aminopeptidase, chymopapain, bromelin and proteolytic enzymes that are substantially free of sulfhydryl groups or disulfide bonds.

7. The enzymatic wound composition of claim 6 wherein the proteolytic enzyme is papain.

8. The method of enzymatic wound debridement, consisting essentially of:
   applying to a wound in need of debridement a combination of an anhydrous hydrophilic poloxamer gel and a small but debridement effective amount of one or more proteoplytic enzymes.

9. The method of claim 8 wherein the poloxamer carrier is a block copolymer of ethylene oxide and propylene oxide of the structure:

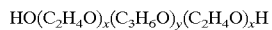

$$HO(C_2H_4O)_x(C_3H_6O)_y(C_2H_4O)_xH$$

wherein x is from 2 to 150, and y is from 15 to 70.

10. The method of claim 9 wherein x is from 12 to 141, and y is from 20 to 56.

11. The method of claim 10 wherein the proteolytic enzyme is used in an amount sufficient to have an activity of from 500 USP units/mg to 3000 USP units/mg.

12. The method of claim 11 wherein the enzymatic activity is from 800 USP units/mg to 2200 USP units/mg.

13. The method of claim 8 wherein the proteolytic enzyme is selected from the group consisting of papain, trypsin, chymo-trypsin, streptokinase, streptodornase, ficin, pepsin, carboxypeptidase, aminopeptidase, chymopapain, bromelin and proteolytic enzymes that are substantially free of sulfhydryl groups or disulfide bonds.

14. The method of claim 13 wherein the proteolytic enzyme is papain.

* * * * *